US00PP13162P2

(12) United States Plant Patent
Michalik

(10) Patent No.: US PP13,162 P2
(45) Date of Patent: Oct. 29, 2002

(54) VARIETY OF GERANIUM PLANT NAMED 'FIWOSAL'

(75) Inventor: Andrea Michalik, Dresden (DE)

(73) Assignee: Elsner pac Jungpflanzen (DE)

( * ) Notice: Subject to any disclaimer, the term of this patent is extended or adjusted under 35 U.S.C. 154(b) by 0 days.

(21) Appl. No.: 09/733,003

(22) Filed: Dec. 8, 2000

(65) Prior Publication Data

US 2002/0073465 P1 Jun. 13, 2002

(51) Int. Cl.[7] ..... A01H 5/00

(52) U.S. Cl. ..... Plt./328

(58) Field of Search ..... Plt./330, 328, 325, Plt./324, 327

*Primary Examiner*—Kent L. Bell

(74) *Attorney, Agent, or Firm*—Webb Ziesenheim Logsdon Orkin & Hanson, P.C.

(57) ABSTRACT

A new and distinct pelargonium plant with star-like, red colored flowers above medium green foliage. The plant is suitable for planting in pots or as a bedding plant.

1 Drawing Sheet

BOTANICAL/COMMERCIAL CLASSIFICATION

*Pelargonium×hortorum*; Zonal Geranium.

VARIETY DENOMINATION

'Fiwosal'.

BACKGROUND OF THE INVENTION

The present invention comprises a new and distinct cultivar of *Pelargonium×hortorum* known by the varietal name 'Fiwosal'. The new variety was discovered in 1996 in a selective breeding program in Dresden, Germany. The new variety is the result of a cross between two unnamed and unpatented selections from breeding group 5K-49, which comprises about 50 steller-type breeding varieties with salmon colored flowers. The new variety has a compact habit whereas its parental cultivars have an irregular habit. The new variety has narrow upper petals but its parental cultivars have wide upper petals. The new variety was first asexually reproduced by cuttings in Dresden, Germany in 1997. The new variety has been trial and field tested and has been found to retain its distinctive characteristics and remain true to type through successive propagations.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. The color readings were taken outdoors in diffuse light during summer. Color references are primarily to The R.H.S. Colour Chart of The Royal Horticultural Society of London. The instant cultivar was 9 months old and in a container having a diameter of 15 cm when described.

PLANT

Form: Erect.
Height from media surface to top of foliage: 45–48 cm.
Height from media surface to top of umbel: 60 cm.
Width: 35–40 cm.
Growth: High degree of branching.
Strength: Does not require artificial support.
Response time: 3.5 weeks.
Leaves:
- *Length.*—4–5 cm.
- *Width.*—5–6 cm.
- *Shape.*—Maple leaf-shaped.
- *Margin.*—Entire; deeply indented.
- *Texture.*—Smooth; some pubescence.
- *Color.*—Upper surface: Green Group 139B with zone of Greyed-Orange Group 166A. Lower surface: Green Group 137D.
- *Ribs and veins.*—Color: Green Group 141B.

Petioles:
- *Color.*—Yellow-Green Group 146D.
- *Length.*—3–5 cm.
- *Diameter.*—0.3 cm.

Stem/branches:
- *Color.*—Yellow-Green Group 147B.
- *Length.*—22 cm.
- *Internode length.*—3–5 cm.

THE BUD

Shape when just showing color:
- *Overall.*—Semi-spherical.
- *Individual bud.*—Narrow; elliptical.

Color: Green Group 143B.
Size when just showing color:
- *Umbel.*—7–9 cm across. Depth of 8 cm.
- *Individual bud.*—1–1.5 cm long; 0.5 cm wide.

INFLORESCENCE

Blooming habit: Free flowering; continuous; single.
Size of fully open bloom: 2–3 cm across.

Average number of inflorescense per plant: 30–50 per season.

Borne: Umbel; flowers on pedicel; pedicel on peduncle.

Flowers:

*Form.*—Zygomorph.

*Number of petals.*—5.

*Size.*—Upper petals: 0.5–0.7 cm wide; 1.5 cm long. Lower petals: 0.7–1.0 cm wide; 1.5 cm long.

*Petals.*—Color: Upper surface: Red Group 52C. Lower surface: Red Group 52D.

*Texture and appearance.*—Velvety.

*Apex.*—Pointed.

*Base.*—Pointed.

*Margin.*—Serrated.

Petaloids: Absent.

Pedicel:

*Length.*—2.5–3 cm.

*Color.*—Green Group 143C in Spring turning to Greyed-Purple Group 184A in Summer.

Peduncle:

*Length.*—12 cm.

*Color.*—Yellow-Green Group 148B.

Sepals:

*Quantity.*—5.

*Shape.*—Lanceolate.

*Length.*—0.6 cm.

*Width.*—0.2 cm.

*Apex.*—Pointed.

*Base.*—Wide (not pointed).

*Margin.*—Smooth.

*Color.*—Upper surface: Yellow-Green Group 146A. Lower surface: Yellow-Green Group 146B.

Disease/pest resistance: No susceptibility to diseases or pests has been noted to date.

Lasting quality: Long-lasting; 3–4 weeks per umbel.

REPRODUCTIVE ORGANS

Stamens:

*Anthers.*—3 mm long.

*Filaments.*—Length: 0.5 cm maximum. Color: Pink.

*Pollen.*—Orange.

Pistils:

*Number.*—One; 5 parted.

*Length.*—0.3–0.4 cm.

*Stigma.*—Red in color.

*Style.*—0.8 cm long.

Ovaries:

*Color.*—Greenish.

*Length.*—0.4 cm.

Fruit: Present with 5 seeds; fruit production very weak.

GENERAL CHARACTERISTICS

1. Maple leaf-shaped foliage.
2. Erect, compact growth.
3. Good branching.
4. Flowers single, star-like.
5. Long-lasting with high resistance against rain.
6. Low care requirements.

I claim:

1. A new and distinct variety of zonal geranium plant substantially as shown and described.

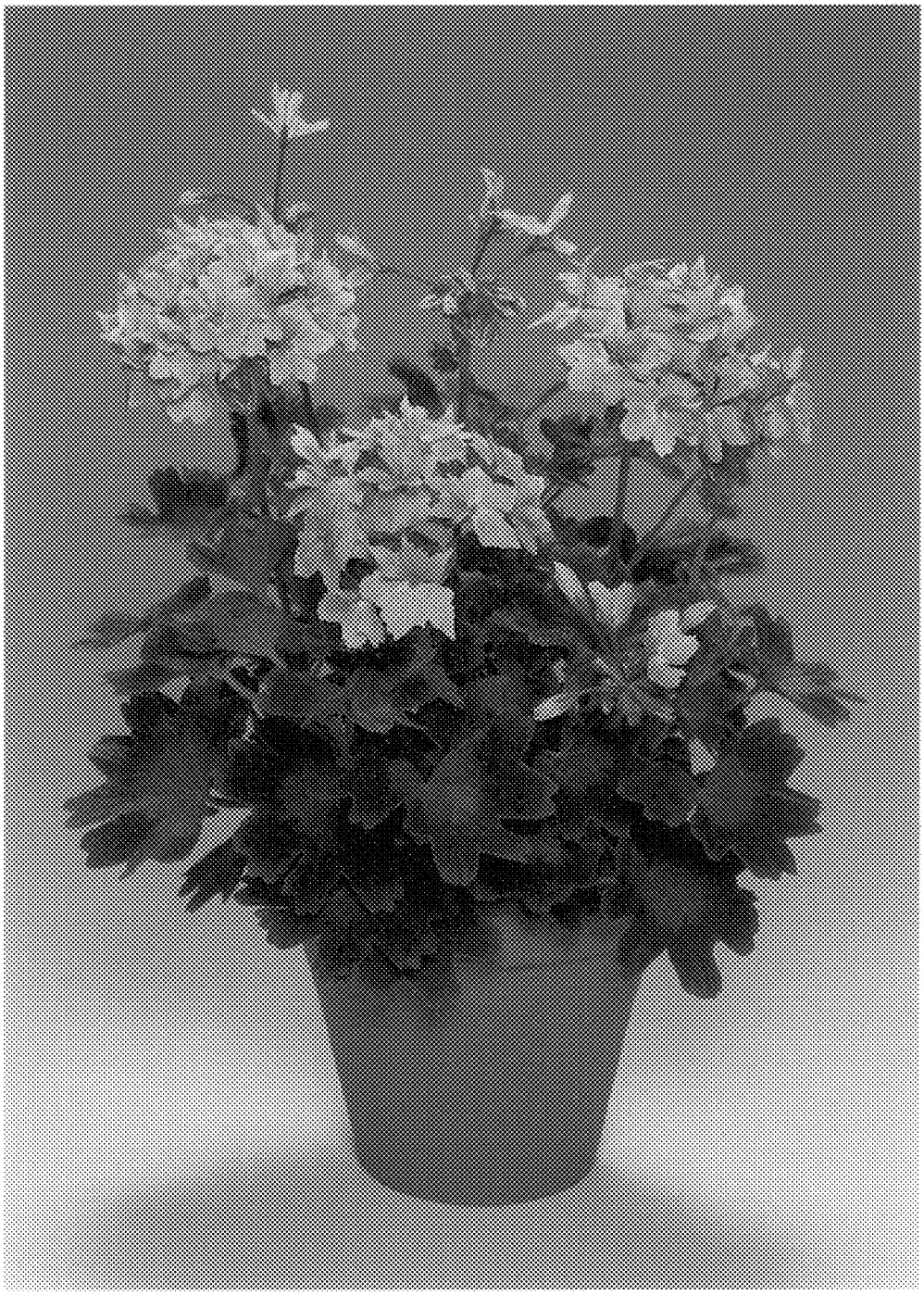

* * * * *